United States Patent [19]

Goble et al.

[11] Patent Number: 5,496,317
[45] Date of Patent: Mar. 5, 1996

[54] LAPAROSCOPIC SURGICAL INSTRUMENT

[75] Inventors: Nigel M. Goble, Castleton; Colin C. O. Goble, Canton, both of United Kingdom

[73] Assignee: Gyrus Medical Limited, United Kingdom

[21] Appl. No.: 237,118

[22] Filed: May 3, 1994

[30] Foreign Application Priority Data

May 4, 1993 [GB] United Kingdom ............ 9309142

[51] Int. Cl.⁶ .................................. A61B 17/00
[52] U.S. Cl. .................. 606/48; 606/46; 128/751
[58] Field of Search .................. 128/749, 751, 128/755; 606/46, 48, 50

[56] References Cited

U.S. PATENT DOCUMENTS

| | | | |
|---|---|---|---|
| 2,032,860 | 3/1936 | Wappler et al. | 606/46 |
| 2,068,721 | 1/1937 | Wappler et al. | 606/98 X |
| 4,674,498 | 6/1987 | Stasz | 128/303.14 |
| 4,721,116 | 1/1988 | Schintgen et al. | 128/751 |
| 4,802,476 | 2/1989 | Noerenberg et al. | 128/303.14 |
| 4,817,630 | 4/1989 | Schintgen et al. | 128/751 |
| 4,850,353 | 7/1989 | Stasz et al. | 128/303.14 |
| 4,958,539 | 9/1990 | Stasz et al. | 76/104.1 |
| 5,074,311 | 12/1991 | Hasson | 128/755 X |
| 5,151,102 | 9/1992 | Kamiyama et al. | 606/51 |
| 5,192,298 | 3/1993 | Smith et al. | 128/751 X |
| 5,201,743 | 4/1993 | Haber et al. | 606/147 |
| 5,217,460 | 6/1993 | Knoepfler | 606/46 X |
| 5,238,002 | 8/1993 | Devlin et al. | 128/751 |
| 5,281,220 | 1/1994 | Blake, III | 606/46 |
| 5,330,471 | 7/1994 | Eggers | 606/46 X |

FOREIGN PATENT DOCUMENTS

| | | | |
|---|---|---|---|
| 0507622A1 | 10/1992 | European Pat. Off. | A61B 17/28 |
| 0518230A1 | 12/1992 | European Pat. Off. | A61B 17/39 |

*Primary Examiner*—Sam Rimell
*Attorney, Agent, or Firm*—Fish & Richardson

[57] ABSTRACT

A laparoscopic surgical instrument which may be in the form of forceps or a cutter has, at the end of a hollow tube for introduction through the body cavity wall, a housing, a pair of pivotally mounted metallic jaws, a reciprocable control rod in the tube, and an actuator secured to the control rod. The actuator has a pair of guide grooves which are oppositely inclined with respect to a longitudinal axis of the instrument, and each jaw has a lug which fits in a respective groove, the lugs being spaced from the jaw pivots so that reciprocation of the control rod causes opening and closing of the jaws. The housing and the actuator are electrically insulating and the jaw pivots are spaced apart to achieve electrical isolation of one jaw from the other, for applying a radio frequency voltage across the jaws for bipolar electrosurgery.

28 Claims, 5 Drawing Sheets

LAPAROSCOPIC SURGICAL INSTRUMENT

This invention relates to a laparoscopic surgical instrument having a pair of jaws which are pivotable with respect to each other.

A disposable laparoscopic instrument of the above description is disclosed in EP-A-0507622. Mounted at the end of a tube for insertion into the body cavity is a pair of jaws pivotable with respect to each other about a common pivot axis in a scissor action. The jaws are actuated by a push rod in the tube, the end of the push rod being connected beyond the end of the tube by a pair of links to proximally directed extensions of the jaws so that reciprocation of the push rod causes pivoting of the jaws.

Being a laparoscopic instrument, this prior device is designed to be introduced through a so-called "keyhole" aperture or port placed in the wall of the body cavity using a trocar. For minimal tissue damage such ports are made as small as possible with typical port sizes being in the range of from 5 mm to 12.5 mm and, as a result, the instrument suffers from disadvantages arising out of the compact construction necessary to allow the jaws and their actuating mechanism to be passed through a narrow trocar, particularly a limitation on the force which can be applied by the jaws and distortion of the mechanism during use.

The problems faced by the designer of a laparoscopic instrument are compounded if electrosurgical energy is to be applied. In open surgical procedures, bipolar electrosurgery is most commonly used with forceps applicators. As the tissue to be treated is in close proximity to the hand of the operator, the forceps are constructed as long arms insulated and hinged at the rear. Each arm of the forceps is connected to the active and return output lines of an the electrosurgery radio frequency (RF) generator. In this fashion, all tissue within the grasp of the forceps may be desiccated. The most useful application of bipolar forceps is in stemming blood flow from cut vessels. They are particularly useful in this application because the blood vessel may be closed by applying closure pressure to the forceps before activating the RF output. During activation, the inner walls of the vessel become tacky and therefore stick together whilst the blood within the vessel forms a coagulum. Thus blood loss from severed blood vessels may be quickly staunched.

The delivery of electrosurgical energy by a laparoscopic instrument is of particular advantage when parting or dissecting tissue. This is a difficult operation when performed remotely and hidden blood vessels are easily ruptured, which means that it is advantageous to be able to use one and the same instrument for cauterisation, i.e. using RF energy, or desiccation prior to dissection. Due to the need to be able to apply a controllable opening force for the dissection action, scissors or graspers are favoured which, by their nature, tend to be used for monopolar application of RF energy. Laparoscopic instruments for bipolar electrosurgery have to date relied upon modifying conventional designs. One known instrument makes use of two forceps arms resiliently biased apart at a point close to the working ends. Closure of the forceps is achieved by passing an outer tube over the sprung arms to urge them together. The main drawback of this design is that there is no controllable opening force other than the weak force provided by the spring. This prevents use of the device as a dissector, a fact which has to date limited the exploitation of bipolar techniques.

According to one aspect of this invention, a laparoscopic surgical instrument comprises a tube for introduction into the body cavity; a housing at the end of the tube; a pair of jaws extending distally from the housing, at least one of the jaws being pivotally mounted on the housing to allow pivotal opening and closing movements with respect to the other jaw about a transverse pivot axis; an elongate control member extending inside the tube and reciprocable longitudinally with respect to the tube and the housing, and an actuator at a distal end of the control member and reciprocable therewith; wherein the actuator has a guide track and the at least one pivotally mounted jaw has a guide track follower spaced from the pivot axis and engaging the guide track, and wherein the guide track is so oriented that longitudinal reciprocating movement of the actuator is converted into pivotal movement of the said at least one jaw about the pivot axis. The instrument may be a pair of forceps with the jaws formed for grasping tissue, or it may be a cutting device with the jaws shaped as blades or as a blade and anvil combination. Preferably, both jaws are pivotally mounted on the housing and both are connected to the actuator, the latter being located between the jaws distally of their pivotal mountings.

To convert reciprocating motion into pivotal motion the or each pivotal jaw may be connected to a head part of the actuator by means of the combination of a respective guide track angled with respect to the direction of reciprocation of the control rod and a guide track follower slidable along the track, the track preferably being associated with the actuator, and the follower with the respective jaw. In this way the track may extend to opposite sides of the centre line of the control rod for maximum transverse travel of the guide follower. Conveniently, the track is a groove or slot which slidably houses a follower in the form of a peg or pin. In one preferred embodiment the actuator head part and connecting elements (i.e. pegs or pins) of the jaws are outside the confines of the tube and in the space between the opened jaws. This yields a very good range of movement of the jaws with, as a result, lower forces in the mechanism as a whole than would be needed if all movement was to be confined within a 5 mm tube, for example. In particular, by having the actuator part which bears the guide track or tracks movable in a region between, on the one hand, the jaw mounting pivots and, on the other hand, the ends of the jaws, a more robust jaw structure and jaw mounting can be obtained for a given size compared with, e.g., scissor-action jaws in which the jaws are driven from an actuator located proximally of the pivots. The lateral extent and the angle of the guide track respectively determine the range of movement of the jaw and the mechanical advantage of the mechanism. While the preferred embodiments have a straight guide track, it may be curved to alter the mechanical advantage for different jaw positions, e.g. allowing closure pressure on a ruptured vessel to be increased without suffering a decrease in the range of movement. The mechanism allows a reciprocating action to be used to apply both opening and closing forces from the handgrip. In embodiments in which both jaws are pivotable, the actuator is a longitudinally reciprocable element with one guide track inclined in one angled orientation relative to the direction of movement, and another guide track inclined in a different or oppositely angled orientation so that as the actuator is moved the peg or pin of one jaw moves in opposite direction to the peg or pin of the other jaw. The tracks are preferably formed on opposite faces or sides of the actuator.

The above constructions are particularly suited to bipolar forceps for electrosurgery, each jaw being formed from a metallic material and connected to supply conductors associated with the tube, with both the housing and the actuator being formed of an electrically insulating material such as plastics. In the case of both jaws being pivotable, the pivots on the housing maybe spaced apart as a means of maintaining electrical isolation between the jaws. The use of plastics in the mechanism is made possible due to the relatively low forces permitted by the design of the mechanism, allowing the jaws to be insulated in an inexpensive and simple manner.

Bipolar electrosurgical cutters may be similarly constructed bringing the same advantages of electrical isolation and the ability positively to drive the jaws not only together but also apart.

According to a second aspect of the invention, there is provided a laparoscopic surgical instrument comprising: a tube for introduction into the body through an aperture in the body cavity wall, a housing at the end of the tube, pair of jaws extending distally from the housing, at least one of the jaws being pivotally mounted on the housing to allow opening and closing movements with respect to the other jaw, a control member reciprocable in the tube, and an actuator at the end of the control member, which actuator has a movement converter part located between the jaws and distally of the pivotal mounting of the at least one pivotally mounted jaw on the housing, and operable to convert reciprocating movement of the control member into a pivoting movement of the jaw.

The invention also includes, according to a third aspect thereof, a laparoscopic electrosurgical instrument comprising: a tube for introduction into the body through an aperture in the body cavity wall; a housing at the end of the tube; a pair of jaws extending distally from the housing, each jaw having an electrically conductive portion, and at least one of the jaws being pivotally mounted on the housing to allow pivotal opening and closing movements with respect to the other jaw about a transverse pivot axis; an elongate control member extending inside the tube and reciprocable longitudinally with respect to the tube; actuator means coupled to a distal end of the control member and to the said at least one jaw for converting longitudinal reciprocating movement of the control member into pivotal movement of the said at least one jaw about the pivot axis; means for electrically insulating one jaw from the other; and electrical supply conductors respectively coupled to the electrically conductive portion of the jaws, at least one of the conductors being located inside the tube; wherein each of the jaws has an inner surface which, when the jaws are in a closed position, engages the inner surface of the other jaw, and wherein each inner surface is formed by conductive surface parts of the conductive portion of the respective jaw and by at least one intervening insulative surface part (C), the arrangement of the conductive and insulative parts on the two jaws being such that in the closed position of the jaws, the conductive surface parts of one jaw are adjacent, but do not touch, the conductive surface parts of the other jaw. The jaws may comprise a pair of blades arranged to execute a shearing action, the inner surfaces being the surfaces of the blades which face each other when the blades are in a closed position and which are bounded by respective interengaging cutting edges. The conductive and insulative surface parts should preferably extend to the cutting edges, and around the edges.

The invention will now be described by way of example with reference to the drawings in which.

A first preferred embodiment of the invention now to be described is a pair of laparoscopic forceps capable of being used for bipolar electrosurgery. The instrument has a pair of hinged forceps jaws mounted at the end of a shaft in the form of a tube which passes through a trocar fitted in the wall of the body cavity, and at the outer end of the tube there is a hand grip connected to an RF generator. The shaft is typically 280 to 360 mm in length. It is to be understood that this description and the accompanying drawings relate to that part of the instrument which is used inside the body cavity. It is also to be understood that the forceps jaws may instead be the blades of a cutter.

Figure 1:
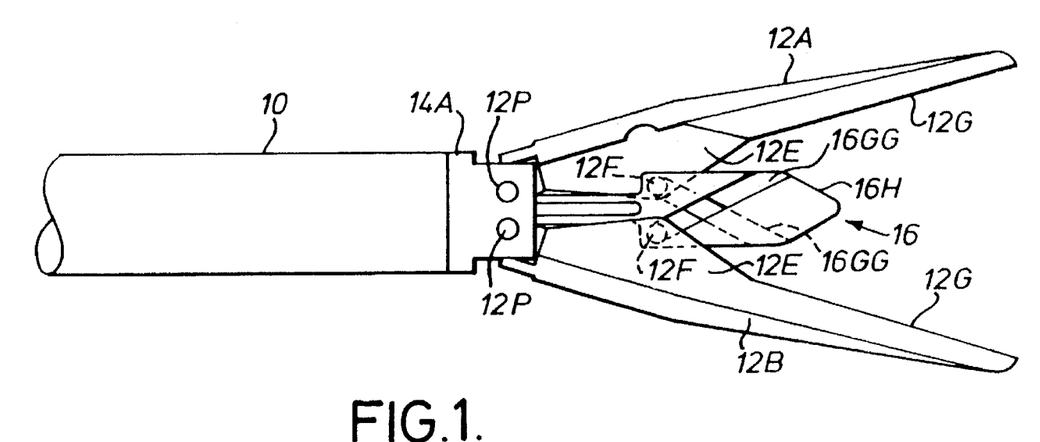
FIG. 1 is a plan view of laparoscopic forceps in accordance with the invention, shown with open jaws.
Figure 2:
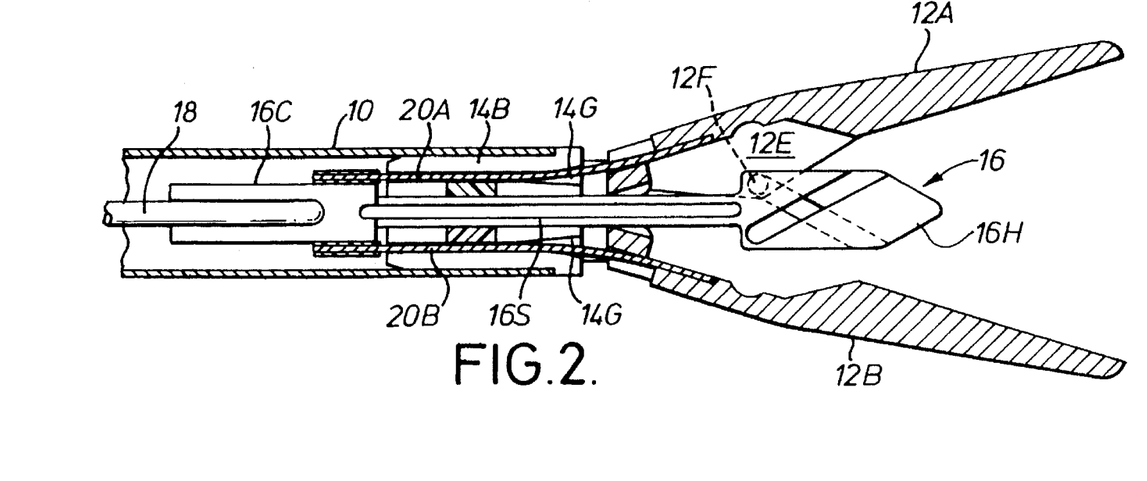
FIGS. 2 is a partly longitudinally sectioned plan view corresponding to FIG. 1.
Figure 3:
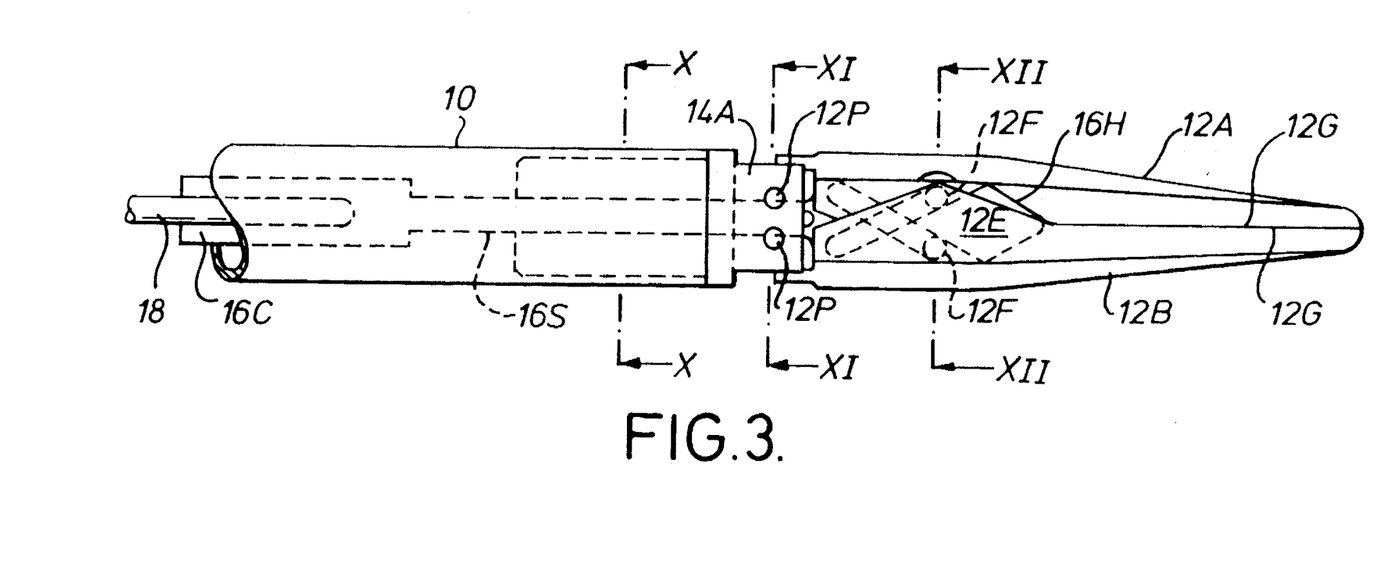
FIG. 3 is a plan view of the forceps with the jaws closed.
Figure 4:
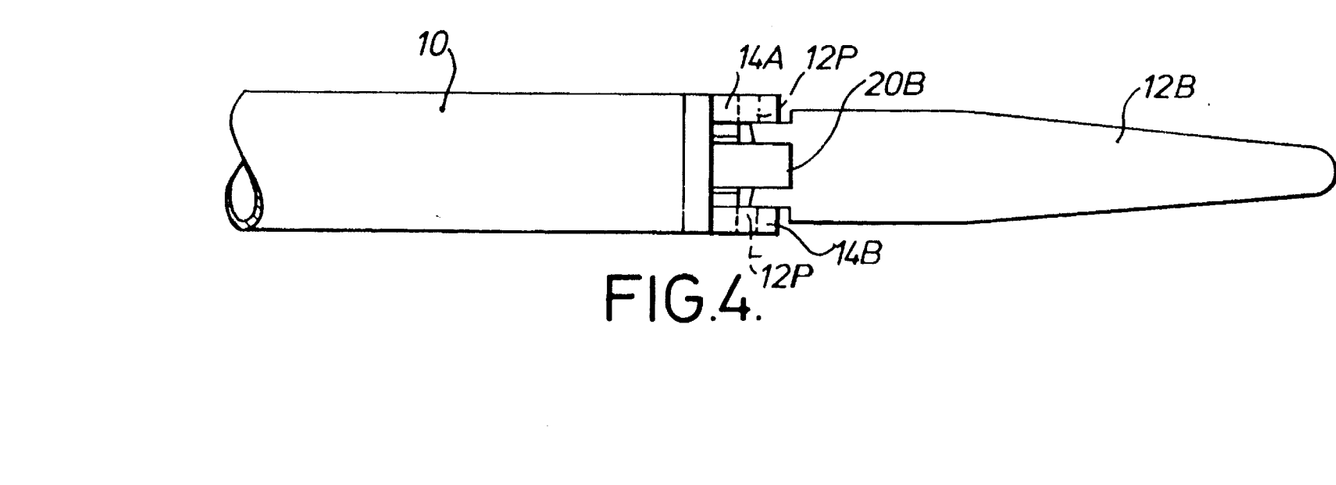
FIG. 4 is a side view of the forceps.

Referring to FIGS. 1 to 4 of the drawings, the instrument shaft, in the form of a stainless steel tube 10, has mounted at its end a pair of steel forceps jaws 12A, 12B. Each jaw is independently pivoted at its proximal end on a jaw housing comprising two plastics collet halves 14A, 14B fitted in the end portion of the tube 10, and is pivotable between open and closed positions by a plastics actuator 16 having an actuator head 16H located between the jaws 12A, 12B distally of their pivots, and an actuator shaft 16S passing between the collet halves 14A, 14B and connected to a control rod 18 of approximately 1 mm in diameter which runs the length of the tube 10 for connection to the hand grip (not shown). In FIGS. 1 and 2 the jaws are shown in their open position. In FIG. 3 they are shown in their closed position.

Also located in the tube 10 are two electrical supply conductors 20A, 20B which, although shown only in part in FIG. 2, extend the length of the tube 10. They are free to twist in the main part of the tube 10 to allow for rotation of the forceps with respect to the hand grip. Each conductor comprises a stainless steel strip having heatshrink insulation where it passes through the tube 10. Grooves 14G are provided in each of the collet halves 14A, 14B for receiving the conductors which pass distally out of the collet into recesses of the jaws 12A, 12B where they are welded to the material of the jaws. Details of the jaws 12A, 12B are seen more clearly in FIGS. 5, 6, and 7.

Figure 5:
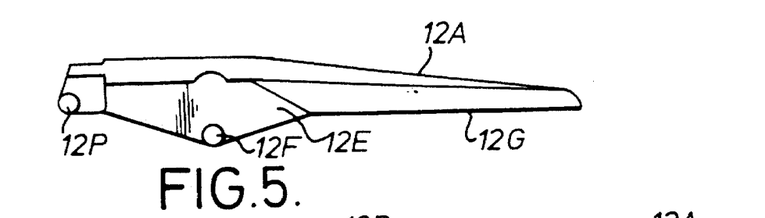
FIG. 5 is a plan view of one of the jaws of the forceps.
Figure 6:
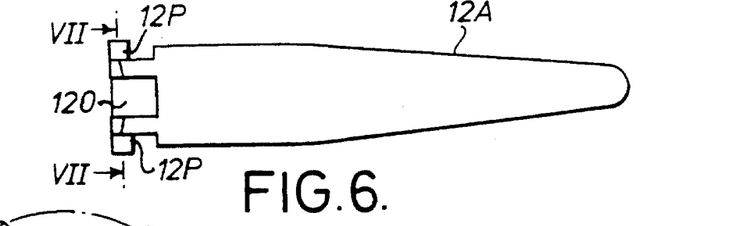
FIG. 6 is an outer side view of the jaw.
Figures 7, 8, 9:
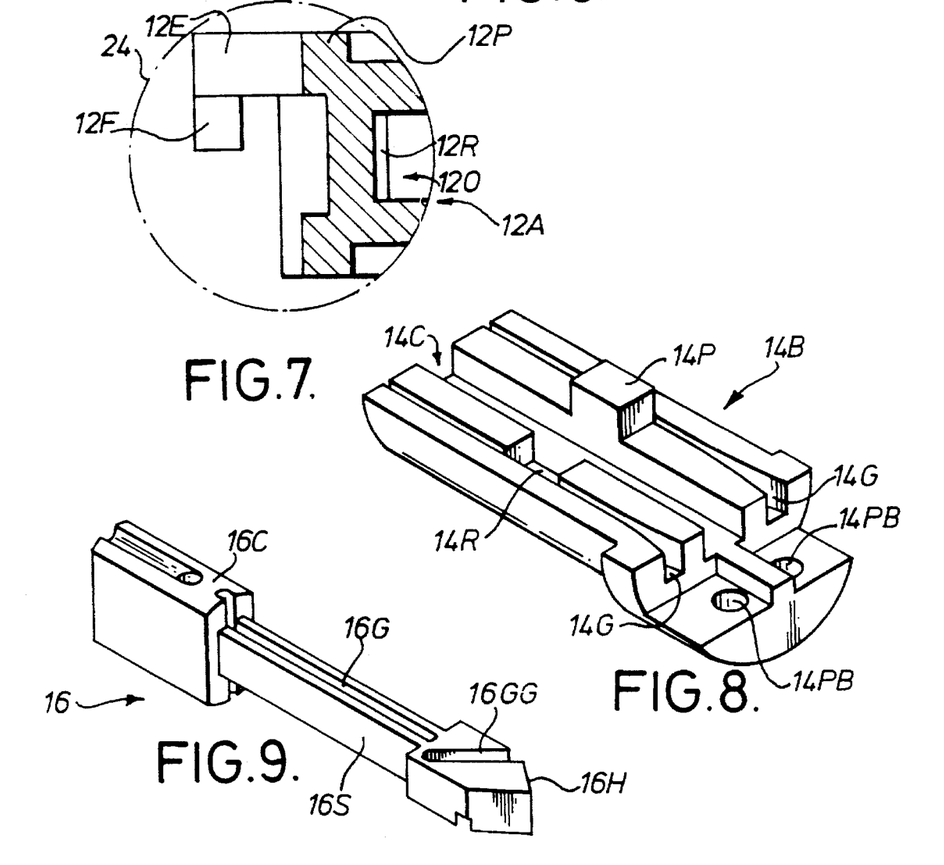
FIG. 7 is a cross-section of the jaw along the line VII—VII in FIG. 6.
FIG. 8 is a perspective view of one half of a jaws housing.
FIG. 9 is a perspective view of an actuator of the forceps.

Referring to FIGS. 5, 6, and 7, each jaw 12A, 12B is a single metal injection moulding of stainless steel 304, coated with an insulating compound such as PTFE on substantially all surfaces except the grasping face 12G and the electrical connection area of an inwardly facing recess 12R which opens into an outer recess of the jaw 12A as shown in FIGS. 6 and 7. The coating prevents accidental cautery of tissue adjacent the operation site. Each jaw comprises a distally tapered body which has, at its proximal end two projecting hinge pins 12P each of which defines a common off-centre hinge axis perpendicular to the longitudinal axis of the instrument and is received in a corresponding bore 14PB in one of the collet halves 14A, 14B (see FIG. 1). The collet halves are so formed that the hinge pins 12P of the jaws 12A,

12B are mounted immediately adjacent the end of the tube 10 for rigidity. Intermediate its ends, each jaw has an inwardly extending ear 12E which is spaced from the longitudinal axis and has an inwardly directed actuation peg 12F for engaging a guide groove in the actuator 16, as will be described below. With regard to their external shape, the jaws are shaped and dimensioned to fit within the circular envelope 24, shown in FIG. 7, corresponding to the outer profile of the tube 10 when the jaws are closed, so that the complete instrument can be passed through a trocar having a corresponding internal diameter. The grasping surfaces 12G are planar and the jaws are mounted so that these surfaces meet in face-to-face contact.

Referring to FIG. 8 in conjunction with FIG. 1, the collet 14A, 14B has three main functions which are to mount the jaws 12A, 12B pivotally in an electrically insulating manner, to house the actuator 16 in a slidable fashion, and to house the electrical conductors 20A, 20B. The two collet halves 14A, 14B are identical, and one of them is shown in FIG. 8. Each half has a part-cylindrical body having an external diameter corresponding to the internal diameter of the tube 10. It mates with the other collet half by planar surface-to-surface contact along a diameter, longitudinal interlocking being provided by corresponding projections and recesses 14P, 14R. A central internal channel 14C slidably houses the shaft 16S of the actuator 16 and the narrow grooves 14G house the conductors 20A, 20B. At the distal end, the collet half is of increased diameter, having a shoulder which abuts the end of the tube 10 and provides a pivot housing of segment-shaped cross-section penetrated by two bores 14PB for housing one pivot pin 12P of each of the jaws 12A, 12B. It will be noticed that the axes of the bores 14PB are off-centre on opposite sides of the centre line of the instrument, thereby spacing the jaws apart for electrical insulation.

The actuator 16 is shown more clearly in FIG. 9 from which it will be seen that the actuator head 16H is of rectangular cross-section and has in one of its faces a guide track in the form of a guide groove 16GG which is inclined with respect to the longitudinal axis of the instrument and which extends on both sides of that axis. A similar, but oppositely inclined groove is formed in the oppositely directed face of the head 16H, as shown by dotted lines in FIGS. 1 and 2. Each groove receives a respective guide peg 12F of One of the jaws 12A, 12B. At the other end of the shaft 16S is a connector 16C for receiving the control rod 18 (see FIGS. 2 and 3) whereby the actuator 16 can be reciprocated to cause the jaws 12A, 12B positively to open and close. The pushing and pulling forces on the control rod 18 are converted into lateral forces on the pegs 12F of the jaws, i.e. corresponding jaw closing and opening forces. One optional feature shown in FIG. 9 is the provision of an irrigation groove 16G in the shaft 16S of the actuator 16 so that irrigation fluid pumped into tube 10 can be introduced for cleaning the forceps and for washing the operative site.

Figures 10, 11, 12, 13:
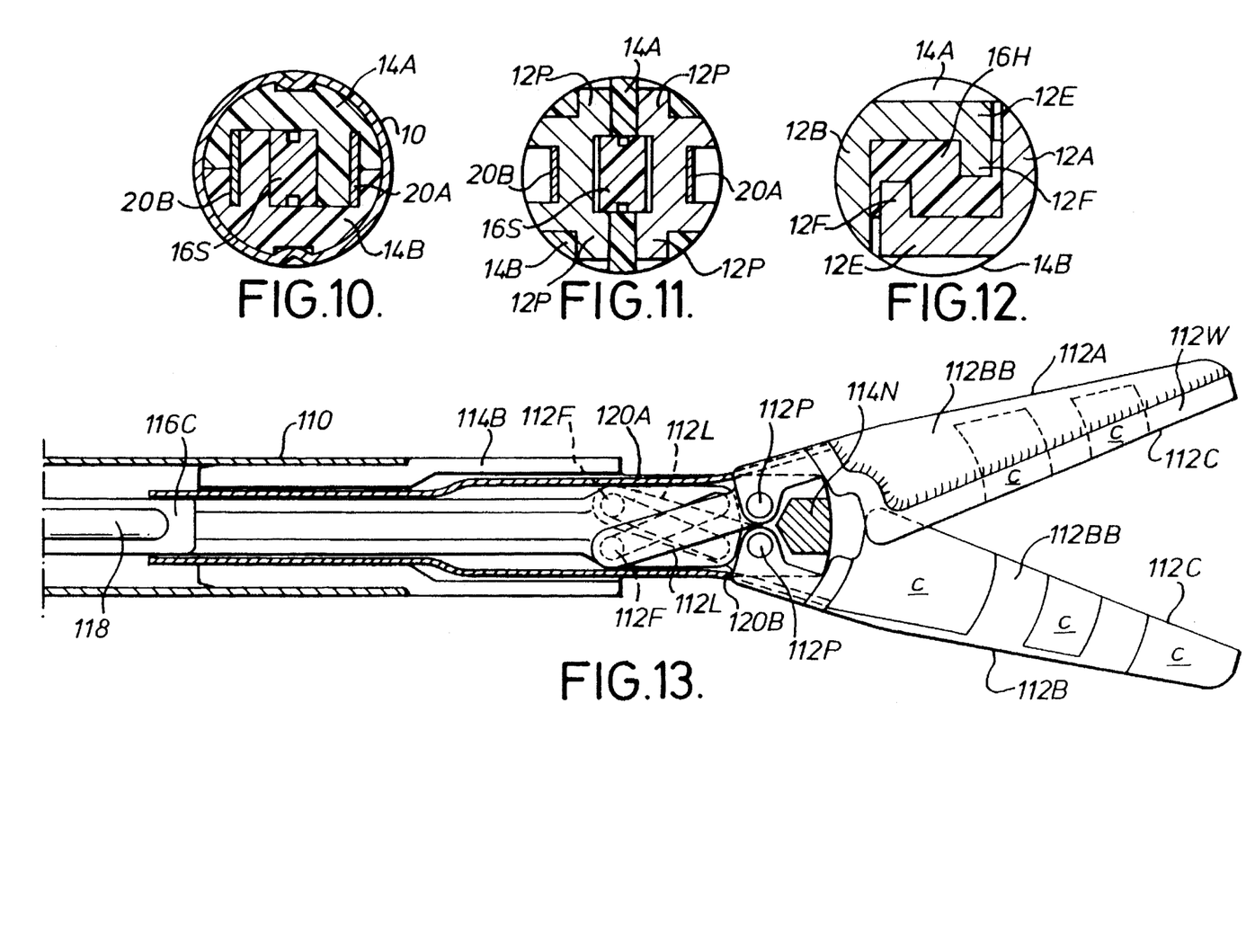
FIG. 10 is a cross-section on the line IX—IX in FIG. 3.
FIG. 11 is a cross-section on the line X—X in FIG. 3.
FIG. 12 is a cross-section on the line XI—XI in FIG. 3.
FIG. 13 is a partly longitudinally sectioned plan view of a laparoscopic cutter in accordance with the invention, shown with the jaws open.

FIGS. 10, 11 and 12 of the drawings are included to aid understanding of the configurations of the components of the instrument. It will be seen particularly from FIG. 12 which shows the forceps with the jaws in the closed configuration, that the actuator 16 substantially completely fills the gap between the two jaws 12A, 12B when the latter are in the closed configuration. Indeed, the jaws, when closed, provide an approximately rectangular-section cavity matching the external dimensions and shape of the actuator head 16H so that the internal surfaces of the jaws which are perpendicular to the pivot axes defined by the pins 12P slide on the oppositely directed upper and lower faces of the actuator head 16H to prevent the torsional closure forces arising by virtue of the offset location of the guide pegs 12F from causing the two jaws from twisting and thereby causing a mismatch at the distal ends of the jaws when they are closed. The effects of torsional forces are also restricted by the wide spacing of the hinge pins 12P of each jaw on either side of the longitudinal axis, and the corresponding spacing of the inwardly directed faces and bores 14PB of the collet halves 14A, 14B. Another property of the interfitting arrangement of the jaws and the actuator head 16H is that when the instrument is first inserted into the body cavity, the likelihood of tissue being trapped is much reduced.

The instrument may be used with a generator having a variable output impedance and frequency, such as that disclosed in British Patent Specification No. 2214430 which is operable typically at voltages in the region of 150 volts.

Figure 14:
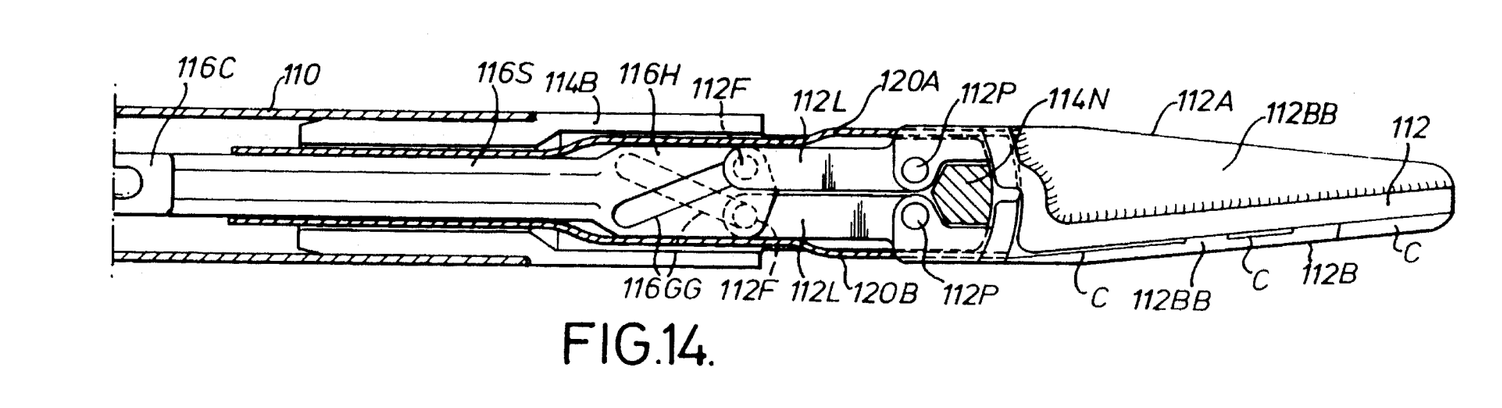
FIG. 14 is a view similar to that of FIG. 13, but with the jaws closed.
Figure 15:
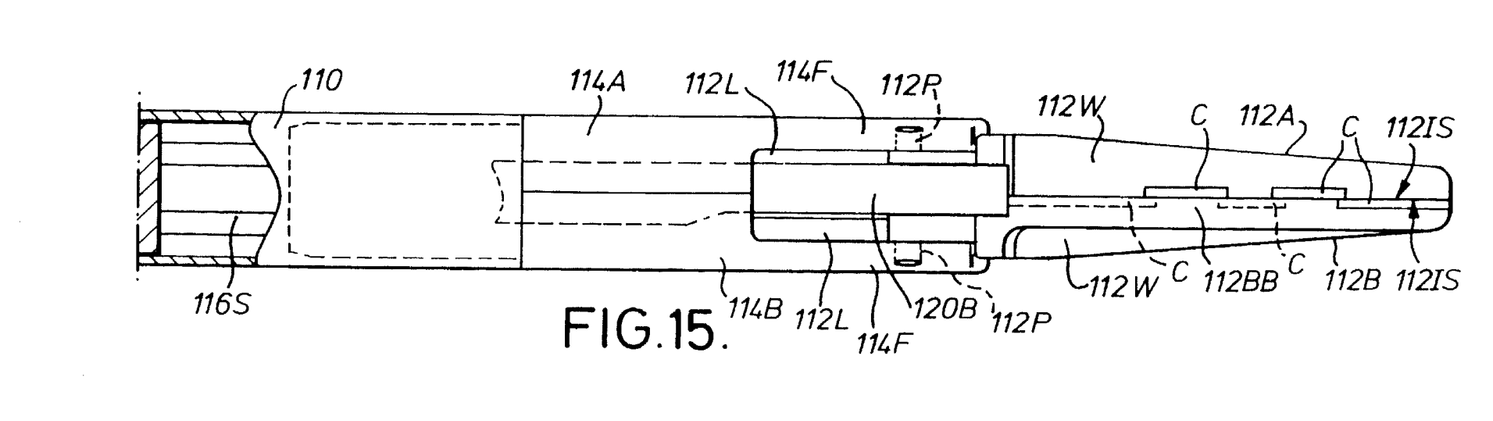
FIG. 15 is a side view of the cutter with the jaws closed.

In some circumstances it may be preferable to locate the actuator proximally of the jaw pivots in the collet. Referring now to FIGS. 13 to 15, a second embodiment of the invention, like the first forceps embodiment described above, has a stainless steel tube 110 as an instrument shaft with, mounted at its end, a pair of steel jaws (112A, 112B). In this case the jaws are in the form of cutter blades 112A, 112B, but the proximal actuator could be used with forceps jaws. As before, each jaw is independently pivoted at its proximal end on a jaw housing comprising two plastics collets halves 114A, 114B fitted in the end portion of the tube 10. In this case, however, an electrically insulative plastics actuator 116 is slidably mounted in the collet halves with an actuator head 116H located proximally of the pivot pins 112P of the blades 112A, 112B. Each blade 112A, 112B, has a proximally extending lever arm 112L with guide track followers 112F located in respective guide grooves or slots 116GG (FIG. 14) of the actuator head 116H. As in the previous embodiment, these grooves 116GG are located on opposite upper and lower faces of the actuator head 16H and are oriented in the same way, i.e. inclined with respect to the direction of movement of the actuator 116 and extending on both sides of the centre line of the actuator, the inclinations being in respective opposite directions so that as the actuator is moved longitudinally, the lever arm 112L of one blade is urged laterally in one direction, while the lever arm 112L of the other blade is moved in the opposite lateral direction, causing the blades to execute a pivoting opening or closing movement according to the direction of movement of the actuator head. Again, as before, the jaws 112A, 112B are positively driven in both open and closing movements by the longitudinal forces applied to the actuator 116 via a control rod 118.

In the embodiment shown in FIGS. 13 to 15, the lever arms 112L stay within a 5 mm overall diameter, i.e. the diameter of the tube 110, when the blades 112A, 112B are in the fully opening configuration, as will be seen from FIG. 13. In an alternative embodiment however, the actuator head 116H may be wider than shown to the extent that it may be exposed at the sides of the instrument over the whole of its range of movement so as to be much closer to the cylindrical envelope defined by the tube 110 and extended distally from the tube. Furthermore, and more importantly, each guide track follower 112F may be positioned on the side of its lever arm 112L which faces inwardly of the instrument when the lever arms 112L cross over as in FIG. 13, to the extent that the lever arms 112L project beyond the cylindrical envelope in the open configuration of the blades. In effect the followers 112F are asymmetrically located on the lever arms. As a result, a greater range of pivoting movement of the blades 112A, 112B can be obtained which can be advantageous in some circumstances.

The collet 114, comprising collet halves 114A, 114B, is, in this embodiment, longer than the collet of the first embodiment. Each collet half 114A, 114B is, as before, mounted in the tube 110 but has an elongate part cylindrical portion extending beyond the distal end of the tube 110 and further extending distally in a finger portion 114F which mount the blades 112A, 112B. Each blade 112A, 112B has a pair of pivot pins 112P which locate in bores in the collet finger portions 114F (see FIG. 15). The finger portions 114F have outer surfaces which, like the outer surfaces of the part cylindrical portions of the collet halves, define, at least in part, an outer cylindrical envelope of the instrument with a diameter suitable for passing through a narrow trochar. The jaws 112A, 112B are mounted between the finger portions 114F of the collet halves 114A, 114B, with the finger portions 114F having a U-configuration when viewed in side elevation (see FIG. 15). In this embodiment, the ends of the finger portions 114F are connected together by respective inwardly extending nose projections 114N, visible in FIGS. 13 and 14. The nose portions 114N are bonded or otherwise held together distally of the jaw pivot pins 112P.

The arrangement of the collet halves 114A, 114B together with the positioning of the actuator head 116H on the actuator shaft 116S, is such that when the actuator head 116H is in a position corresponding to the open configuration of the blades 112A, 112B, it is partly exposed on either side by being located between the collet finger portions 114F. Thus, over at least part of its range of movement the part of the actuator 116 which converts longitudinal movement into pivoting movement moves in a space between the collet halves which is open to the sides, i.e. in directions perpendicular to the pivot axes of the jaws. The position of the actuator head 116H in this instance is shown in FIG. 13. When a pulling force is exerted on the control rod 118 and the actuator connector 116C, the actuator head 116H is withdrawn from its position between the collet finger portions 114F to a position in which it is enclosed in the part cylindrical collet portions which, in this embodiment, extend from the end of the tube 110 to the finger portions 114F, as shown in FIG. 14.

Electrosurgical RF power can be applied to the blades 112A, 112B via respective flexible conductor strips 120A, 120B which extend through the tube 110 from a power source (not shown) to welded connections on the blades 112A, 112B. As with the forceps jaws of the first embodiment, the blades 112A, 112B are so mounted as to be electrically isolated from each other, the collet halves 114A, 114B and the actuator 116 being formed of electrically insulating plastics material so that bipolar electrosurgical energy may be applied. To avoid short circuiting between the blades 112A, 112B, each blade has insulative surface parts as well as conductive surface parts. By way of explanation, it will be seen by comparison of FIGS. 13, 14, and 15 with each other that the blades 112A, 112B are mounted so as to execute a scissor-action. Each blade is generally L-shaped in cross-section, having a blade body 112BB which extends generally perpendicularly with respect to the axis of rotation defined by the pivot pens 112P and a reinforcing web 112W extending outwardly from the blade body 112BB in a direction generally parallel to the said axis. Each blade body has a generally planar inner surface 112IS which, in this embodiment, lie substantially in a common plane intersecting the longitudinal axis of the instrument. The inner surfaces 112IS face and engage each other when the blades are in the closed position (see FIG. 15). The inner surfaces 112IS terminate, in each case, in a cutting edge 112C (see FIG. 13), these edges executing a shearing action when the blades are closed. To prevent electrical shorting, the inner surface 112IS of each blade 112A, 112B has insulative surface parts formed by insulative ceramic inlays which are shown by the letter "C" in FIGS. 13 to 15. These inlays C are arranged in an alternating pattern along the length of each blade 112A, 112B, and are situated so that the intervening conductive surface parts of each blade are in registry with the ceramic inlays C of the other blade when the blades are in their closed configuration. In fact, the extent of each ceramic inlay C in the longitudinal direction of each blade is a little greater than the longitudinal extent of the matching conductive surface part of the other blade so that the ceramic inlays C overlap as shown in FIG. 15 when the blades are closed. The insulative surface part to conductive surface part relationship between the inner surfaces 112IS of the blades 112A, 112B is maintained across the whole of the interengaging parts of the inner surfaces 112IS, each ceramic inlay C extending beyond the coverage of the overlying blade when the blades are in the closed configuration, as shown in FIG. 14. Preferably, the outer surfaces of the blades, i.e. the outer surfaces remote from the cutting edge 112C, in each case are covered with an insulating coating to avoid unwanted cauterisation of tissue outside the blades.

In use, the blades 112A, 112B may have RF electrical energy applied to them for cauterising tissue trapped between the cutting edges 112C providing, of course, the tissue in question contacts conductive parts of both blades.

As an alternative to the interleaved configuration of insulative and conductive surface areas described above, it is possible to arrange for one of blades 112A, 112B to have all of its inner surface 112IS coated with an insulative material with the coating extending to a limited degree around the cutting edge 112C, while the other blade has, over at least the major part of its inner surface 112IS, no such coating so that substantially the whole of the inner surface and the cutting edge are conductive. A cauterisation or desiccation current path can be established between the remaining exposed conductive material of the first above-mentioned blade and the conductive material in the region of the cutting edge of the second above-mentioned blade.

What is claimed is:

1. A laparoscopic surgical instrument comprising:

a tube for introduction into the body through an aperture in the body cavity wall;

a housing at the end of the tube;

a pair of jaws extending distally from the housing, at least one of the jaws being pivotally mounted on the housing to allow pivotal opening and closing movements with respect to the other jaw about a transverse pivot axis;

an elongate control member extending inside the tube and reciprocable longitudinally with respect to the tube and the housing, and an actuator at a distal end of the control member and reciprocable therewith;

wherein the actuator has a guide track, and the at least one pivotally mounted jaw has a guide track follower spaced from the pivot axis and engaging the guide track, and wherein the guide track is so oriented that longitudinal reciprocating movement of the actuator is converted into pivotal movement of the said at least one jaw about the pivot axis; and wherein each jaw has an electrically conductive portion coupled to a respective electrical supply conductor at least one conductor of which is located in the tube, and wherein the actuator is formed of an electrically insulative material.

2. An instrument according to claim 1, wherein both jaws are pivotally mounted on the housing, the actuator has a pair of guide tracks, and each jaw has a respective guide track follower engaging a respective one of the guide tracks, the guide tracks being so oriented that longitudinal reciprocating movement of the actuator is converted into opposing pivotal movements of the jaws.

3. A laparoscopic surgical instrument comprising:
   a tube for introduction into the body through an aperture in the body cavity wall;
   a housing at the end of the tube;
   a pair of jaws extending distally from the housing, at least one of the jaws being pivotally mounted on the housing to allow pivotal opening and closing movements with respect to the other jaw about a transverse pivot axis;
   an elongate control member extending inside the tube and reciprocable longitudinally with respect to the tube and the housing, and
   an actuator at a distal end of the control member and reciprocable therewith;
   wherein the actuator has a guide track, and the at least one pivotally mounted jaw has a guide track follower spaced from the pivot axis and engaging the guide track, and wherein the guide track is so oriented that longitudinal reciprocating movement of the actuator is converted into pivotal movement of the said at least one jaw about the pivot axis; and
   wherein both jaws are pivotably mounted on the housing about respective spaced apart transverse pivot axes.

4. An instrument according to claim 3, wherein the housing is made of an insulative material.

5. An instrument according to claim 1, wherein the jaws are forceps jaws.

6. An instrument according to claim 1, wherein the jaws are the blades of a cutter.

7. An instrument according to claim 1, wherein the jaws comprise a cutter blade and a cutter anvil.

8. An instrument according to claim 1, wherein the actuator has a head part, the guide track being formed on the head part, and wherein the head part is located distally of the said pivot axis.

9. An instrument according to claim 1, wherein the guide track extends both longitudinally and laterally.

10. An instrument according to claim 9, wherein the guide track is a slot.

11. An instrument according to claim 9, wherein the actuator has a head part and the guide track is formed on the head part, and wherein the head part is outside of the tube.

12. An instrument according to claim 3, wherein each jaw has an electrically conductive portion coupled to a respective electrical supply conductor at least one of which is located in the tube, and wherein the actuator is formed of an electrically insulative material.

13. An instrument according to claim 3, wherein the actuator has a pair of guide tracks, and each jaw has a respective guide track follower engaging a respective one of the guide tracks, the guide tracks being so oriented that longitudinal reciprocating movement of the actuator is converted into opposing pivotal movements of the jaws.

14. An instrument according to claim 3, wherein the jaws are forceps jaws.

15. An instrument according to claim 3, wherein the jaws are the blades of a cutter.

16. An instrument according to claim 3, wherein the actuator has a head part, the guide track being formed on the head part, and wherein the head part is located distally of the said pivot axis.

17. An instrument according to claim 3, wherein the guide track extends both longitudinally and laterally.

18. An instrument according to claim 17, wherein the guide track is one of a slot and groove.

19. An instrument according to claim 17, wherein the actuator has a head part and the or each guide track is formed on the head part, and wherein the head part is outside the confines of the tube.

20. An instrument according to claim 9, wherein the guide track is a groove.

21. A laparoscopic surgical instrument comprising a tube for introduction into the body through an aperture in a body cavity wall,
   a housing at the end of the tube,
   pair of jaws extending distally from the housing, at least one of the jaws being pivotally mounted on the housing to allow opening and closing movements with respect to the other jaw,
   a control member reciprocable in the tube, and
   an actuator at the end of the control member, which actuator has a movement converter part located within an opening between the jaws and distally of the pivotal mounting of the at least one pivotally mounted jaw on the housing, and is operable to convert reciprocating movement of the control member into a pivoting movement of the jaw.

22. An instrument according to claim 21, wherein each jaw has an electrically conductive portion coupled to a respective electrical supply conductor at least one conductor of which is located in the tube, and wherein at least the movement converter part of the actuator is formed of an electrically insulative material.

23. An instrument according to claim 22, wherein the housing is made of an insulative material.

24. An instrument according to claim 21, wherein both jaws are pivotally mounted on the housing, the actuator movement converter part has a pair of guide tracks, and each jaw has a respective guide track follower engaging a respective one of the guide tracks, the guide tracks being so oriented that longitudinal reciprocating movement of the actuator is converted into opposing pivotal movements of the jaws.

25. An instrument according to claim 24, wherein the jaws are pivotable on the housing about respective spaced apart transverse pivot axes.

26. A laparoscopic electrosurgical instrument comprising:
   a tube for introduction into the body through an aperture in the body cavity wall;
   a housing at the end of the tube;
   a pair of jaws extending distally from the housing, each jaw having an electrically conductive portion, and at least one of the jaws being pivotally mounted on the housing to allow pivotal opening and closing movements with respect to the other jaw about a transverse pivot axis;
   an elongate control member extending inside the tube and reciprocable longitudinally with respect to the tube;
   actuator means coupled to a distal end of the control member and to the said at least one jaw for converting longitudinal reciprocating movement of the control member into pivotal movement of the said at least one jaw about the pivot axis;
   means for electrically insulating one jaw from the other; and
   electrical supply conductors respectively coupled to the electrically conductive portion of the jaws, at least one of the conductors being located inside the tube;

wherein each of the jaws has an inner surface which, when the jaws are in a closed position, engages the inner surface of the other jaw., and wherein each inner surface is formed by conductive surface parts of the conductive portion of the respective jaw and by at least one intervening insulative surface part, the arrangement of the conductive and insulative parts on the two jaws being such that in the closed position of the jaws, the conductive surface parts of one jaw are adjacent, but do not touch, the conductive surface parts of the other jaw.

27. An instrument according to claim 26, wherein the jaws comprise a pair of blades arranged to execute a shearing action, and wherein the said inner surfaces are surfaces of the blades which face each other when the blades are in a closed configuration and which are bounded by respective interengaging cutting edges, the said conductive and insulative surface parts extending to the cutting edges.

28. An instrument according to claim 26, wherein the conductive and insulative surface parts of each jaw are in an alternating relationship along the length of the jaws, and wherein the conductive surface parts of each jaw are in registry with the insulative surface parts of the other jaw when the jaws are in their closed configuration.

* * * * *